United States Patent [19]

Griswold

[11] Patent Number: 5,658,276

[45] Date of Patent: Aug. 19, 1997

[54] HEATED CRYOSURGICAL PROBE

[75] Inventor: Thomas A. Griswold, Ellington, Conn.

[73] Assignee: Brymill Corporation, Vernon, Conn.

[21] Appl. No.: 407,729

[22] Filed: Mar. 20, 1995

[51] Int. Cl.$^6$ ................................................ A61B 17/36
[52] U.S. Cl. ................................ 606/24; 606/20; 606/23
[58] Field of Search ............................................ 606/20–26

[56] References Cited

U.S. PATENT DOCUMENTS

| | | | |
|---|---|---|---|
| 3,270,744 | 9/1966 | Katz et al. | 606/24 |
| 3,298,371 | 1/1967 | Lee | 606/24 |
| 3,439,680 | 4/1969 | Thomas, Jr. | 606/24 |
| 3,948,269 | 4/1976 | Zimmer | 606/24 |
| 3,971,383 | 7/1976 | Van Gerven | 606/24 |
| 4,116,199 | 9/1978 | Bryne | 606/22 |
| 4,411,266 | 10/1983 | Cosman | 606/49 |

*Primary Examiner*—Angela D. Sykes
*Assistant Examiner*—Michael Peffley
*Attorney, Agent, or Firm*—M. P. Williams

[57] ABSTRACT

Cryosurgical probe tips (20,66) are in metallurgical contact with coils of insulated resistor wire (27, 27a) with one end connected through copper wire (75) to a pin (32) insertable into a switch (33, 34, 51–61) of a battery pack (35–50) which may be clipped (64) to cryosurgical apparatus (9–14), and the other end connected through cryogen liquid feed tube structure (19, 19a) and the cryosurgical apparatus to the other end of the battery pack.

7 Claims, 2 Drawing Sheets

HEATED CRYOSURGICAL PROBE

TECHNICAL FIELD

This invention relates to cryosurgical probes having heaters integrally formed therein, that are easily interchanged with a source of liquid nitrogen and a source of electric power.

BACKGROUND ART

The use of cryosurgical probes for necrotizing lesions is well known. When using a probe to freeze wet tissue, such as in the mouth or the cervix, cryoadhesion results from a thin layer of ice forming between the tissue and the probe surface, adhering to each, and bonding them together. In devices which use the expansion of warm gas (Joule-Thompson principle) to achieve cooling, it has been known to circulate warm gas in order to create a thaw cycle, after freezing. However, the extent of freezing which is achievable utilizing warm gases (such as nitrous oxide) is inadequate in many instances.

Cryogenic devices which spray liquid nitrogen, substantially in the liquid phase, directly on inner surfaces of closed probes and vent the gas therefrom, are far more effective for necrotizing lesions than the devices which use warm gas cycles. However, there is no warm gas to circulate in order to provide a thaw to break the cryoadhesion. In most modern cryosurgery, hand-held units utilizing dewars of on the order of a half liter or less are generally employed. These devices typically use a variety of probes which are detachably affixed thereto as required. This presents the problem of providing a thaw cycle to a detachable probe.

When using liquid nitrogen or other cryogenic gases, the degree of freezing is quite extensive, thereby requiring significant heat in order to create an adequate thaw to break the cryoadhesion. However, in many applications, the probe may be inserted within a body cavity, thereby making it imperative that parts of the body which are not to be necrotized are not damaged either by freezing or by burning. This presents the problem of providing adequate heat to relieve the cryoadhesion while at the same time not creating additional hazard from the heat.

DISCLOSURE OF INVENTION

Objects of the invention include provision of cryosurgical probes which utilize liquid cryogenic gas applied directly to an inside surface thereof having means to provide a thaw cycle that can relieve cryoadhesion, and relieving cryoadhesion on interchangeable probes of a liquid cryogenic instrument.

This invention is predicated on the discovery that cryoadhesion can be broken by applying heat directly to the surface of a probe without raising the temperature of any part of the probe to a degree that would pose a hazard to surrounding, healthy tissue.

According to the present invention, a length of insulated resistive wire is coiled in contact with the metallic structure of a hollow cryosurgical probe, the inner surfaces of which are chilled by the direct spray of liquified cryogenic gas in substantially the liquid phase. In accordance with the invention, the resistive wire is fed current from small batteries through a single wire at one end, the other end of the resistive wire being connected to the opposite end of the battery power through the structure of the probe and the cryogenic unit. According to the invention, the coil of resistive wire may be flat or it may be a spiral. It may comprise PFA Teflon® coated constantan.

Other objects, features and advantages of the present invention will become more apparent in the light of the following detailed description of exemplary embodiments thereof, as illustrated in the accompanying drawing.

BEST MODE FOR CARRYING OUT THE INVENTION

Figure 1:
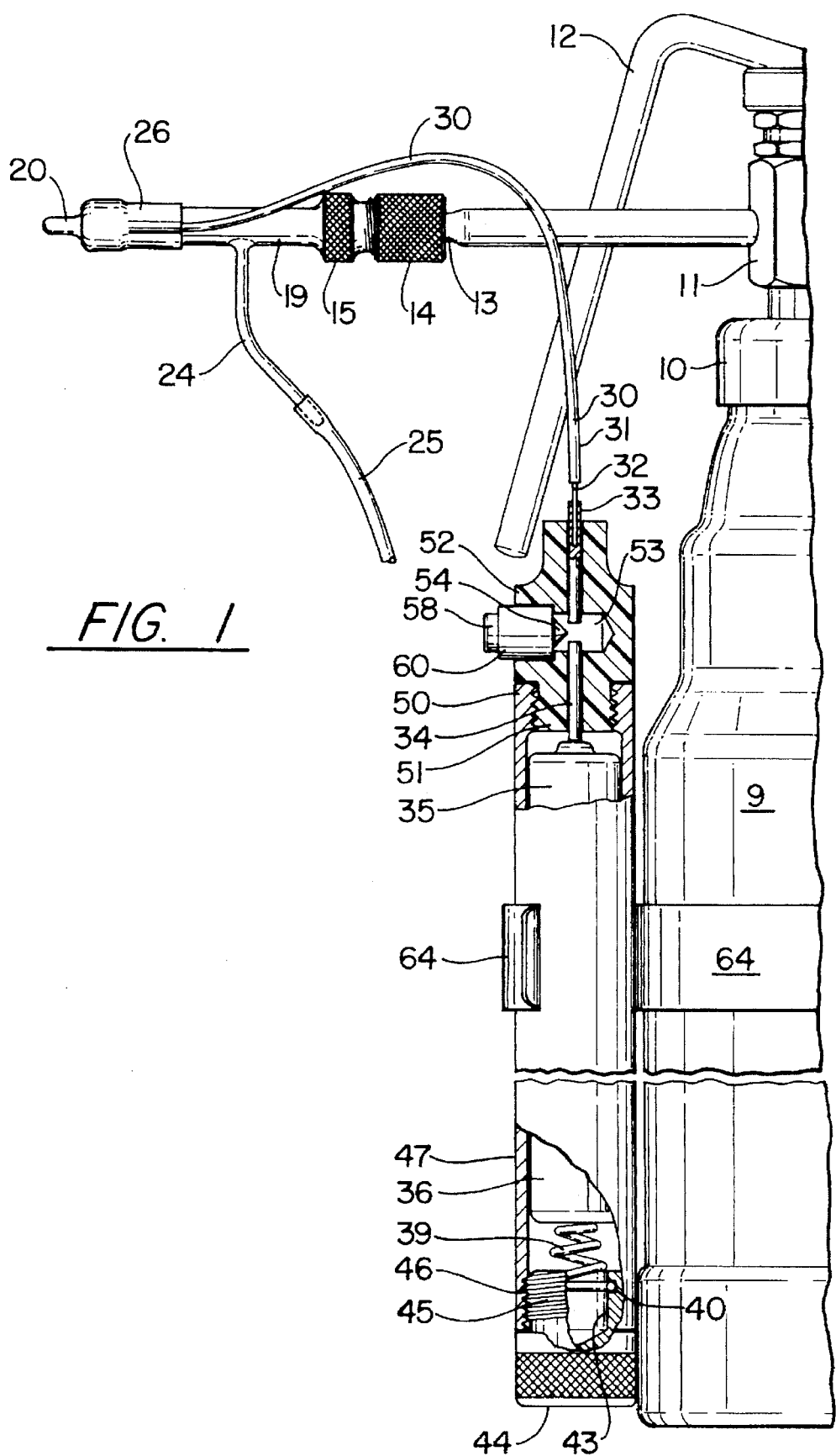
FIG. 1 is a partial, partially sectioned, partially broken away side elevation view of a first heated probe according to the invention mounted on a cryosurgical unit.
Figure 2:
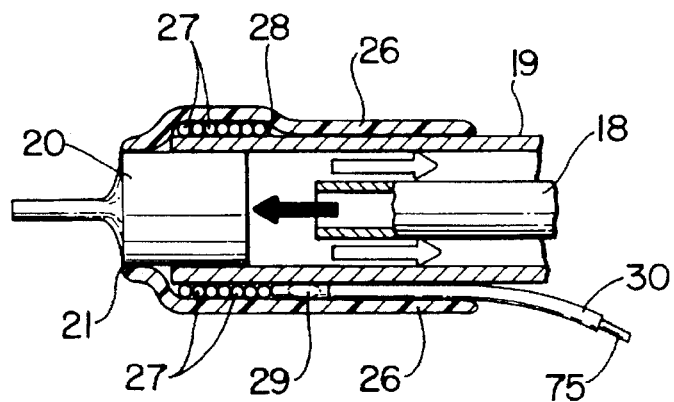
FIG. 2 is a partial, partially sectioned, partially broken away, top plan view of the probe shown in FIG. 1.

Referring now to FIG. 1, a known cryosurgical instrument, of the type shown in U.S. Pat. No. 4,269,390, includes a dewar 9 having a cap 10 fastened thereto, there being a valve 11 operated by a handle 12 disposed in the cap 10. As is known, the valve 11 communicates with liquid cryogen near the bottom of the dewar 9 by means of a tube. When the valve 11 is opened, liquid nitrogen flows through a tube 13 to a knurled female threaded fitting 14, into which a knurled male threaded fitting of a probe is releasably attached. The fitting 15 has two tubes bonded to it, the inner tube (FIG. 2) 18 being a liquid delivery tube which is bonded to the aperture in the fitting 15, so that any liquid flowing to the fittings 14, 15 passes through the interior of the tube 18. Surrounding the tube 18 is a tube 19 which is bonded to the fitting 15 coaxially with the tube 18. A probe tip 20, which may be brass or other good heat conductor, is metallurgically bonded such as with silver solder, at the juncture 21 between the probe tip 20 and the tube 19. Liquid flowing in the tube 18 impinges on the probe tip 20 (as shown in FIG. 2 by the solid arrow), bringing it quickly to nearly liquid nitrogen temperature (−196° C., −318° F.), causing the liquid to vaporize and flow outwardly in the annulus between the two tubes 18, 19 (as shown by the open arrows) to a vent tube 24, over which a plastic hose 25 may be placed to lead the vapor away from the patient and the surgeon using the instrument. The tip 20 may have an adhesion-resisting coating, such as teflon, typically.

According to the invention, a heater is formed outside the probe tip 20 by a coil of resistive wire 27 which is coated with a suitable insulator such as PFA Teflon®. One end of the resistive wire is soldered to the tube 19, such as at the point 28. The other end of the resistive wire is soldered to a length of copper wire 75 at a point 29 with all of the copper wire and some portion of the PFA coated resistive wire being covered with heat shrink tubing 30 so as to insulate it from the tube 19. The coil of resistive wire 27, the solder joint 29, and some portion of the copper wire 75 covered with heat shrink plastic is altogether shrouded in a larger piece of heat shrink plastic 26. In FIG. 1, the other end of the copper wire is soldered (such as at a point 31) to a brass contact pin 32 which is inserted into a central bore of a brass upper switch contact 33. The upper switch contact 33 comprise a brass rod about 180 mils in diameter, with about a 60 mil hole therein to receive the pin 32. A similar (but solid) lower switch contact pin 34 makes contact with the positive end of a battery 35. Depending upon the manner of use, two or three batteries may be used. The lowermost battery 36 has its negative pole contacted by a conical spring 39 that is lightly captured in an annular notch 40 formed within a cavity 43 of a plug 44. The plug 44 may be made of a single piece of aluminum, for instance, if desired. The plug has a reduced portion with male threads 45 that engage female threads 46 formed inside a housing 47 that may comprise a thick wall aluminum tube having an OD of about ¾ inch and an ID of about 9/16 inch. The upper end (as seen in FIG. 1) of the tube 47 is similarly threaded at 50 to receive male threads of a threaded reduced portion 51 of a switch plug 52 within which the upper and lower switch contacts 33, 34 are press fit. The switch body 52 may preferably comprise Delrin® or a suitable form of Teflon® or Nylon®. The switch contacts 33, 34 are separated within a chamber 53 of the switch body 52; electrical contact between them is made by means of a brass conical switch contact 54.

Figure 3:
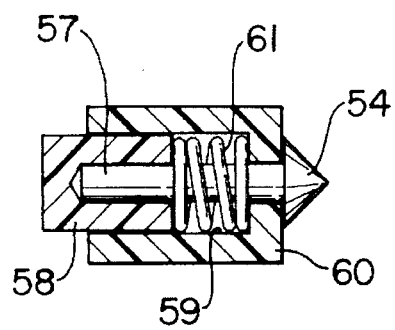
FIG. 3 is a partly sectioned side elevation view of a switch for use with the heated probe of FIG. 1.

In FIG. 3, the conical switch contact 54 is formed in one piece with a shank 57 which is press fit into a switch button 58. The switch button 58 is free to slide within a chamber 59 formed in a cylindrical housing 60. Within the chamber 59, a spiral compression spring 61 urges separation between the right end of the chamber 59 as seen in FIG. 3 and the switch button 58. This tends to cause the cone 54 and switch button 58 to have the position relative to the housing 60 as seen in FIG. 3. However, forcing the switch button 58 to the right as seen in FIG. 3 will compress the spring and cause the cone 54 to extend outwardly to the right. The housing 60 is press fit into an enlarged portion of the chamber 53 so that it does not move with respect to the switch plug 52. When the switch button 58 is pressed, the cone 54 competes the circuit between the switch contacts 33, 34 and causes current to flow through the tip 32, and the copper wire 75 (within the insulation 30) through the resistive wire 27 and into the tube 19. Current then flows through the fittings 14, 15, the tube 13, and the other structure of the cryogenic apparatus 9-11, to one or more clips 64 which hold the tube 47 adjacent the dewar 9. The clips 64 may comprise S-straps, a small bight of which engages the tube 47 and a large bight of which engages the dewar 9. This will allow removing the electrical apparatus 33-64 from the dewar 9, when not in use.

Figure 4:
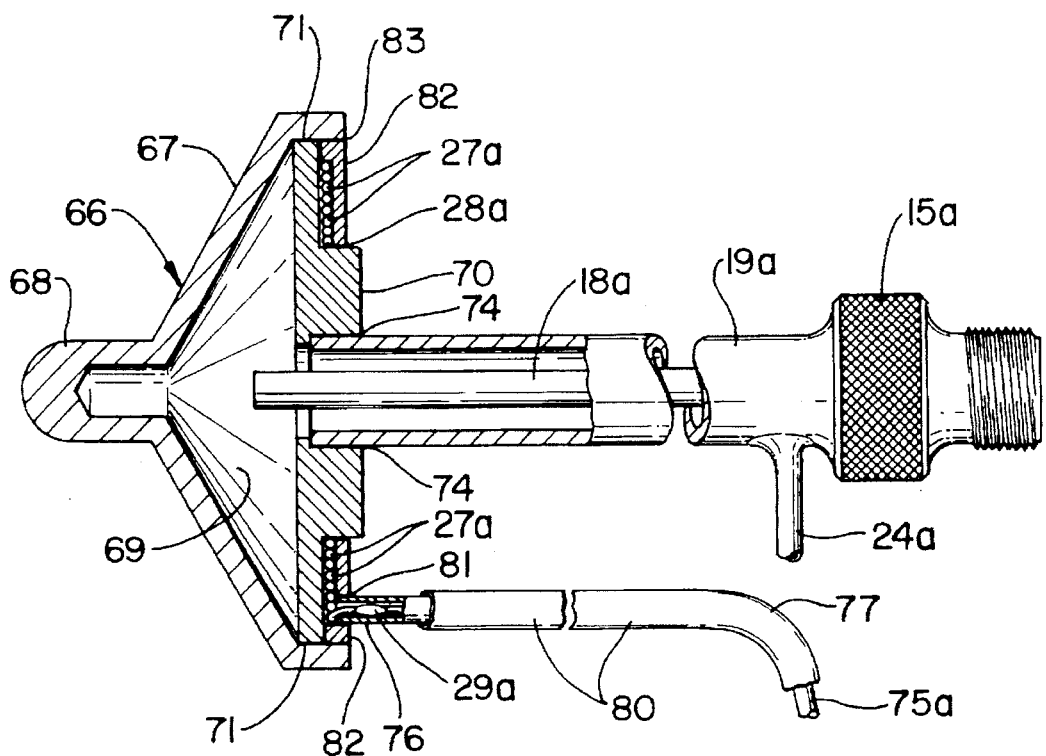
FIG. 4 is a partial, partially sectioned, partially broken away, side elevation view of a second heated probe in accordance with the present invention.

The manner of treatment for a much larger probe is illustrated in FIG. 4. Therein, parts which are essentially the same as those of FIGS. 1 and 2 bear the same reference numerals with an "a" suffix, and need not be described further. However, the coil 27a is flat, rather than a spiral. The probe of FIG. 4 is designed for use in treatment of the cervix. The tip 66 thereof has a generally conical portion 67 with a rounded knob 68 at the apex thereof, and may typically have an adhesion-resistive coating. The conical portion 67 is closed so as to form a chamber 69 by means of a large stepped washer 70 which can be suitably bonded, such as by silver soldering at its perimeter 80 to the tip 66. It is also metallurgically bonded to the tube 19a at its interior circumference 74. Thereafter, the resistance wire is soldered near the boss of the step washer 70 at 28a and wrapped into a flat coil, being connected with copper wire 75a at the point 29a, covered with thin shrink fit plastic to insulate it, and inserted through a small stainless steel tube 76. The tube 76 leads backward to a point 77 about alongside the fitting 15a, after which the copper wire 75 is free to traverse any path. The tube 76 and copper wire 75 are encased in shrink fit plastic 80. The tube 76 is metallurgically bonded, such as with soft solder, into a hole 81 within a small dished-out washer 82, the entire perimeter of which is bonded to the probe tip 66, with soft solder, such as at 83.

The embodiments of FIGS. 2 and 4 illustrate how the resistive wire 27, 27a may be coiled differently. Of importance in practice of the present invention is the fact that the resistive wire itself is separated from metal to which the probe tip is metallurgically bonded by no more than a thin layer (such as PFA Teflon® coating) which provides the necessary low voltage electrical insulation. In the embodiment of FIG. 4, both of the stepped washers 70, 82 conduct heat radially outwardly to the probe tip 66. As used herein, the term "metallic probe structure" means the probe tip 20, 66 itself, and the adjacent metal 19, 70 and 82, metallurgically bonded thereto and in the direct vicinity of the probe tip 20, 66. In FIG. 2, the resistive wire 27 could be wound directly around the tip 20, if the tip were long enough to provide sufficient room. However, it is found that the arrangement shown in FIG. 2 is quite adequate. Since the conduction of heat is a function of the temperature differential, most of the heat provided by the resistive wire coil 27, 27a will be conducted to the cold probe tip 20, 66 rather than to the tube 19, 19a.

Non-resistive wire, such as copper wire, is used to connect the coil of resistive wire through the pin to the source of electric power so that the conductor does not get warm. To change from one probe to another, the pin 32 is removed from the bore of the switch contact 33 and the knurled female fitting 14 is turned to unthread it from the knurled male fitting 15. Then, another probe (such as that of FIG. 4) can be positioned so that the knurled fitting 14 can be screwed onto the knurled fitting 15a, and a brass pin (not shown) similar to pin 32 inserted into the bore of the switch contact 33. The invention therefore provides the preferential heat conduction to the probe tip so as to break cryoadhesion without elevating the temperature with respect to adjacent, healthy tissue, and the ability to have exchangeable probes which may be heated. The coils may be comprised of about three inches of ten mil constantan wire, in which case three standard AA size batteries (4.5 volts) may be used as a power source. This will provide about thirty normal thaw cycles.

Thus, although the invention has been shown and described with respect to exemplary embodiments thereof, it should be understood by those skilled in the art that the foregoing and various other changes, omissions and additions may be made therein and thereto, without departing from the spirit and scope of the invention.

I claim:

1. A cryosurgical instrument comprising:
    a liquid cryogen storage and delivery unit having a first fitting for releasably engaging a probe assembly, a dewar, an operator-controlled valve for enabling flow of cryogen from said dewar, and a first feed tube for conducting cryogen from said valve to said fitting;
    a probe assembly comprising a metallic probe structure including a probe tip having a distal surface for contact with tissue to be frozen and having a proximal surface, a coil of insulated resistive wire in thermal contact with said metallic probe structure and one end of which is in electrical contact with said metallic probe structure, said probe assembly also comprising a second fitting for releasably engaging said first fitting and a second feed tube for conducting cryogen from said second fitting to said proximal surface;
    a battery container for holding and making electrical contact with one end of one or more batteries;
    an operator-controlled switch mounted on said container for making electrical contact with the other end of said one or more batteries;
    said probe assembly also comprising a wire connected to the other end of said coil and releasably engageable into electrical conduction with said switch; and means for releasably securing said battery container in electrical conduction with said storage and delivery unit.

2. A cryosurgical instrument comprising:

a liquid cryogen storage and delivery unit having a first fitting for releasably engaging a probe assembly, a dewar, an operator-controlled valve for enabling flow of cryogen from said dewar, and a first feed tube for conducting cryogen from said valve to said fitting;

a probe assembly comprising a metallic probe structure including a probe tip having a distal surface for contact with tissue to be frozen and having a proximal surface, a coil of insulated resistive wire in contact with said metallic probe structure, said probe assembly also comprising a second fitting for releasably engaging said first fitting and a second feed tube for conducting cryogen from said second fitting to said proximal surface;

a battery container for holding and making electrical contact with one end of a plurality of axially aligned batteries, said container mounting an operator-controlled switch for making electrical contact with the other end of said batteries;

said probe assembly also comprising a wire connected to said coil and releasably engaging said switch in electrical conduction therewith; and means for releasably securing said battery container in electrical conduction with said storage and delivery unit.

3. A probe according to claim 2 wherein said coil is flat.

4. A probe according to claim 2 wherein said coil is a spiral.

5. A probe according to claim 2 wherein said coil is formed of constantan wire.

6. A probe according to claim 5 wherein said coil is formed of constantan wire having a diameter on the order of ten mils.

7. A probe according to claim 5 wherein said coil contains about three inches of wire.

* * * * *